United States Patent [19]

Bullard et al.

[11] 4,230,842

[45] Oct. 28, 1980

[54] HYDROCARBON RESIN

[75] Inventors: Herbert L. Bullard, Norton Village; Robert A. Osborn, Stow, both of Ohio

[73] Assignee: The Goodyear Tire & Rubber Company, Akron, Ohio

[21] Appl. No.: 736,635

[22] Filed: Oct. 28, 1976

Related U.S. Application Data

[63] Continuation of Ser. No. 552,690, Feb. 24, 1975, abandoned.

[51] Int. Cl.³ .................................................. C08F 210/08
[52] U.S. Cl. ............................................ 526/185; 525/90; 526/237; 526/308; 526/337; 526/339
[58] Field of Search ..................... 526/185, 237, 339

[56] References Cited

U.S. PATENT DOCUMENTS

| | | | |
|---|---|---|---|
| 3,478,005 | 11/1969 | Wheeler | 526/237 |
| 3,577,398 | 5/1971 | Pace et al. | 526/237 |
| 3,622,551 | 11/1971 | Davis | 526/237 |
| 3,784,530 | 1/1974 | Osborn et al. | 526/237 |
| 3,865,903 | 2/1975 | Nahmias et al. | 526/237 |

*Primary Examiner*—Edward J. Smith
*Attorney, Agent, or Firm*—H. C. Young, Jr.

[57] ABSTRACT

A hydrocarbon-derived, tack enhancing, diolefin/olefin backboned resin prepared by reacting, in the presence of an aliphatic hydrocarbon solvent and a selected catalyst, a monomer mixture comprised primarily of a diolefin/olefin mixture, of the piperylene/olefin type, and about 2 to about 12 weight percent α-methyl styrene.

The resin has a particular application for use as a tackifier with styrene-isoprene-styrene block copolymers.

4 Claims, No Drawings

HYDROCARBON RESIN

This is a continuation of application Ser. No. 552,690 filed Feb. 24, 1975, now abandoned.

This invention relates to synthetic hydrocarbon-derived resins and to their preparation. This invention especially relates to resins suitable for use in pressure sensitive adhesives derived from a manipulative combination of diolefins, olefins and α-methyl styrene.

Valuable resins can be prepared by polymerizing a diolefin/olefin mixture characterized by a principal backbone of piperylene and 2-methyl-2-butene. Such resins, which polymerized with aluminum chloride, are especially valuable for use in adding tack to various rubbers for adhesive purposes.

However, such resins are many times inadequate for effectively enhancing the tack of various unvulcanized block copolymers for pressure sensitive adhesive purposes. Pressure sensitive adhesives demand a tailored balance of cohesive and adhesive forces to yield effective shear, peel and tack values uncommon to ordinary building-tack rubbery materials. Simply increasing the 2-methyl-2-butene, or decreasing the piperylene, content of the backbone has been found to be insufficiently effective in most cases.

Therefore, it is an object of this invention to provide an improved hydrocarbon-derived resin having a primary diolefin/olefin backbone for pressure sensitive tack-imparting purposes.

In accordance with this invention, a hydrocarbon-derived resin, suitable as a rubber tackifier, is prepared by the method which comprises reacting in the presence of an aliphatic hydrocarbon solvent and a catalyst selected from aluminum chloride and ethyl aluminum dichloride, a monomer mixture comprised of 88 to about 98 weight percent of a diolefin/olefin mixture of a weight ratio in the range of about 0.6/1 to about 1.4/1 and, correspondingly, about 12 to about 2, preferably about 9 to about 3, weight percent α-methyl styrene, where said diolefin comprises at least 95 weight percent piperylene and up to about 5 weight percent isoprene based on the diolefin, and where said olefin comprises at least one olefin selected from 2-methyl-2-butene, 2-methyl-1-butene, 2-methyl-2-pentene and 2-methyl-1-pentene, preferably at least about 90 weight percent 2-methyl-2-butene or 2-methyl-2-pentene based on the olefin. A 80° C. to 100° C. softening point is typical.

In the practice of this invention, it is preferred that the diolefin is essentially piperylene and that the olefin is essentially 2-methyl-2-butene.

In further practice of this invention, in order to provide effective enhancement of the tack by the α-methyl styrene, it is required in the resin that, as the amount of α-methyl styrene increases, the diolefin/olefin ratio increases. Thus, for example, as α-methyl styrene increases from 2 percent to 12 percent, the diolefin/olefin ratio should correspondingly increase about 0.6/1 to about 1.4/1. In this regard, it is preferred that the amount of α-methyl styrene ranges from 3 to about 9 weight percent and the diolefin/olefin ratio correspondingly ranges from about 0.8/1 to about 1.1.

The resins of this invention are prepared by reacting the manipulated monomers in the presence of an aliphatic solvent, and aluminum chloride or ethyl aluminum dichloride, at a temperature in the range of about 0° C. to about 100° C., preferably in the range of about 10° C. to about 50° C. The reaction can be conducted batch-wise or as a continuous process. The reaction can be conducted at atmospheric pressure or above or below atmospheric pressure. Generally, the autogenous pressure developed by the reaction can be used.

Representative of various aliphatic solvents are saturated hydrocarbons containing 3 to about 8 carbon atoms, representative of which are n-butane, isobutane, n-pentane, isopentane, n-hexane, isohexane, n-heptane and isoheptane. Hexane and heptane are preferred. It is understood that unreacted hydrocarbons in the polymerization mixture can also act as a solvent. Generally sufficient solvent is used to provide a solution containing 70 weight percent monomers or resin, although higher or lower concentrations can usually be used.

Generally the reaction can be conducted over a period of time in the range of about 30 to about 120 minutes, although shorter or longer times can be used.

The resin is generally recovered by deactivating the catalyst with a material selected from water, an alcohol such as methanol, isopropanol and butanol and/or lime, filtering the product and steam stripping the filtrate to remove volatiles. Then the resin can be mixed with various rubbers as tackifiers.

The resin of this invention has been found to be particularly useful for mixing with unvulcanized elastomeric block copolymers for the purpose of forming pressure sensitive adhesives. Particularly representative of such copolymers are unvulcanized elastomeric block copolymers having the general configuration A-B-A wherein each A is a non-elastomeric polystyrene block having an average molecular weight in the range of about 5,000 to about 30,000 and a glass transition temperature above about 25° C., the total block A content being about 10 to about 50, preferably about 12 to about 30, weight percent of the copolymer and B is an elastomeric polymer block selected from 1,4-addition polymers of isoprene, as a diene polymer, having an average molecular weight in the range of about 50,000 to about 150,000 and a glass transition temperature below about 10° C., said copolymer having a tensile strength at 25° C. in excess of 200 pounds per square inch. Thus, such unvulcanized elastomeric block copolymer comprises non-elastomeric terminal polymer blocks and internal elastomeric polymer blocks. Generally it is preferred that the difference between glass transition temperatures of the end blocks and middle blocks be at least 40° C. and more preferably at least about 100° C.

The block copolymers can conveniently be prepared by first polymerizing styrene with a lithium based initiator. Various lithium based initiators can be used such as, for example, lithium metal, alkyl lithium compounds, lithium hydrocarbyls and organolithium amides. Alkyl lithium compounds are preferred. Particularly preferred are branched chain, preferably secondary, alkyl lithiums. Such alkyl lithiums especially include secondary butyl lithium, isobutyl lithium, isoamyl lithium and secondary amyl lithium.

After polymerizing styrene to an average molecular weight of about 5,000 to about 30,000, the isoprene as the diene monomer and additional amounts of styrene are added to the polymerization mixture. The polymerization is then continued to provide an elastomeric non-conjugated diene polymer block followed by a non-elastomer block polymer of the styrene.

Such a polymerization, to form the block copolymer, is generally conducted at a temperature in the range of about 20° C. to about 65° C. in an inert hydrocarbon solvent such as an aliphatic or aromatic hydrocarbon.

When preparing pressure sensitive adhesives, generally the tackifying resin is mixed with the block copolymer in an amount of about 30 to about 250 weight percent of the tackifying resin, based on the mixture of resin and block copolymer. If desired, the mixture can conveniently be formed by mixing the tackifying resin and block copolymer in the presence of a volatile organic hydrocarbon solvent such as toluene, benzene, hexane, heptane and octane. In this manner, the adhesive mixture, with solvent, is simply applied to a substrate surface, partially drying the application, and contacting said substrate surface with the adhesive mixture therebetween and drying said adhesive.

Alternatively, a pressure sensitive adhesive tape can be provided by applying the resin/block copolymer solution to a flexible substrate and drying the mixture.

The practice of this invention is more fully illustrated by reference to the following example which is intended to be representative rather than limiting of the scope of the invention. Unless otherwise indicated, all parts and percentages are by weight.

EXAMPLE I

A series of experiments was conducted, identified herein as Experiments A-H and Experiment A-A. In these experiments, various amounts of piperylene and 2-methyl-2-butene, along with heptane, were charged to reactors. Additionally, various amounts of α-methyl styrene along with aluminum trichloride were also charged to the reactors. The polymerization reactions were conducted at temperatures in the range of about 27° C. to about 30° C. for about 120 minutes. The catalyst was deactivated with methanol and lime. The resin was simply recovered by filtering the product and steam stripping the filtrate to remove volatiles.

The parameters and results of the experiments A-H are more clearly shown in the following Table 1, as well as the tackifying ability of the resins when mixed with an unvulcanized block copolymer of styrene-isoprene-styrene in an amount of 50 parts resin per 50 parts block copolymer. Note that, as the ratio of piperylene (PIP) to 2-methyl-2-butene (2MB2) is increased, the percent α-methyl styrene must also be increased to achieve the same tack value. It is equally important to note that by operation of this invention, tack values can be maintained while 2-methyl-2-butene content is actually reduced. Experiment A-A is included to more clearly demonstrate that this type of resin has little, if any, effect upon enhancing the tack of a butadiene/styrene-type rubber. Experiment A shows that without α-methyl styrene, the tack is substantially reduced by a great magnitude.

TABLE 1

| Exp | Monomer Ratio Pip/2MB2 | Wt % alpha methyl styrene[2] | Softening Point (°C.)[3] | Tack (Rolling Ball) (inches) |
|---|---|---|---|---|
| A-A[1] | 1.0 | 6.3 | 90.5 | No tack |
| A | 1.0 | 0 | 100.5 | 18.12 |
| B | .6 | 2.9 | 88 | 1.26 |
| C | 1.4 | 3.0 | 98 | 5.93 |
| D | 1.0 | 6.3 | 90.5 | 1.68 |
| E | 1.0 | 6.2 | 92.0 | 1.58 |
| F | .6 | 8.6 | 85.5 | .70 |
| G | 1.4 | 9.1 | 94 | 1.09 |
| H | 1.0 | 12.4 | 88 | .8 |

[1]Experiment A-A used a 1,3-butadiene/styrene emulsion polymerized elastomeric copolymer
[2]Bases on piperylene, 2-methyl-2-butene and α-methyl styrene. The piperylene/2-methyl-2-butene/α-methyl styrene actually, in addition, about 22 percent 2-pentene, 1 percent isoprene, 3.5 percent cyclopentene and 1.5 percent other hydrocarbons containing 5 to 6 carbon atoms.
[3]Ring and Ball softening point (ASTM E 28-58 T)

So long as the basic piperylene/said olefin backbone is maintained, the polymerization monomer mixture can be modified by containing up to about 15 weight percent, preferably only up to about 10 weight percent, piperylene dimers, piperylene trimers, or other unsaturated hydrocarbons containing 5 to 6 carbon atoms. Representative of such hydrocarbons, which may take place in the polymerization reaction, include those, in addition to the 2-methyl-2-butene, selected from 2-methyl-1-butene, 2,3-dimethyl-1-butene, 2,3-dimethyl-2-butene, 2-methyl-1-pentene, 2-methyl-2-pentene, cyclopentene and 1,3-cyclopentadiene. It is understood that other hydrocarbons containing 4 to 6, more generally 5 to 6, carbon atoms can be present which act more as diluents than reactants. Representative of typical hydrocarbons which have been found to be present are 3,3-dimethyl-1-butene, 1-pentene, 2-pentene, 3-methyl-2-pentene, 4-methyl-1-pentene, 2-hexene and cyclohexene.

While certain representative embodiments and details have been shown for the purpose of illustrating the invention, it will be apparent to those having skill in this art that various changes and modifications may be made therein without departing from the spirit or scope of the invention.

What is claimed is:

1. A hydrocarbon-derived, tack enhancing, piperylene/2-methyl-2-butene backboned resin, modified with a minor amount of α-methylstyrene, characterized by having a softening point in the range of about 85° C. to about 100° C. prepared by the method which consists essentially of reacting at a temperature in the range of 10° C. to about 50° C. in the presence of a solvent selected from at least one of hexane, heptane and unreacted hydrocarbons and a catalyst selected from at least one of aluminum chloride and ethylaluminum dichloride, a monomer mixture consisting of about 88 to about 98 weight percent of a diolefin/olefin mixture in a weight ratio in the range of about 0.6/1 to about 1.4/1 and, correspondingly, about 12 to about 2 weight percent α-methylstyrene, where said diolefin is piperylene, optionally modified by containing up to about 5 weight percent isoprene based on the piperylene/isoprene mixture, where said olefin is 2-methyl-2-butene and where said polymerization monomer mixture is optionally modified by containing up to about 10 weight percent of at least one of the group selected from piperylene dimers, piperylene trimers, 2-methyl-1-butene, 2,3-dimethyl-1-butene, 2,3-dimethyl-2-butene, 2-methyl-1-pentene, 2-methyl-2-pentene, cyclopentene and 1,3-cyclopentadiene based on the total monomer mixture.

2. The resin of claim 1 where the diolefin/olefin weight ratio ranges from about 0.8/1 to about 1/1, the α-methylstyrene is correspondingly used in an amount of about 9 to about 3 weight percent.

3. The resin of claim 2, where said resin is recovered from the polymerization mixture by first neutralizing the catalyst with a material selected from water, lime and at least one alcohol selected from methanol, isopropanol and butanol, followed by steam stripping the filtrate to remove volatiles.

4. The resin of claim 3 where said piperylene/2-methyl-2-butene/α-methyl styrene backbone monomers are modified by containing up to about 10 weight percent other unsaturated hydrocarbons containing 5 to 6 carbons.

* * * * *